(12) United States Patent
Leuer et al.

(10) Patent No.: US 9,724,843 B2
(45) Date of Patent: Aug. 8, 2017

(54) CEMENT PRODUCTION SYSTEM

(71) Applicant: ThyssenKrupp Industrial Solutions AG, Essen (DE)

(72) Inventors: Alfons Leuer, Oelde (DE); Heinz Bredemeier, Sassenberg (DE); Michael Streffing, Lippetal-Hovestadt (DE); Klaus Adler, Rheda-Wiedenbruck (DE)

(73) Assignee: ThyssenKrupp Industrial Solutions AG, Essen (DE)

( * ) Notice: Subject to any disclaimer, the term of this patent is extended or adjusted under 35 U.S.C. 154(b) by 253 days.

(21) Appl. No.: 14/440,752

(22) PCT Filed: Nov. 5, 2013

(86) PCT No.: PCT/EP2013/073055
§ 371 (c)(1),
(2) Date: May 5, 2015

(87) PCT Pub. No.: WO2014/072291
PCT Pub. Date: May 15, 2014

(65) Prior Publication Data
US 2015/0265989 A1    Sep. 24, 2015

(30) Foreign Application Priority Data
Nov. 7, 2012  (DE) .................. 10 2012 110 653

(51) Int. Cl.
*B28B 15/00* (2006.01)
*G01N 33/00* (2006.01)
(Continued)

(52) U.S. Cl.
CPC ............... *B28B 15/00* (2013.01); *F27B 7/42* (2013.01); *F27D 19/00* (2013.01);
(Continued)

(58) Field of Classification Search
CPC ............... B01F 15/06; B01F 2015/062; B01F 2215/0047; B28B 15/00; F27B 7/42;
(Continued)

(56) References Cited

U.S. PATENT DOCUMENTS 4,035,193 A * 7/1977 Miyamoto ................ F27B 7/20
106/759
4,110,121 A * 8/1978 Rechmeier .............. C04B 7/443
106/745
(Continued)

FOREIGN PATENT DOCUMENTS

DE        29924941 U1    3/2007
DE   102008036088 A1    2/2010
(Continued)

OTHER PUBLICATIONS

EPO machine translation of JP 4498639 made on Feb. 28, 2017, 10 pages.*

(Continued)

*Primary Examiner* — Tony G Soohoo
(74) *Attorney, Agent, or Firm* — The Webb Law Firm

(57) ABSTRACT

The invention relates to a cement production system with a preheater for preheating the cement raw meal, a calciner for pre-calcining the preheated cement raw meal, and a rotary kiln for firing the pre-calcined cement raw meal, wherein the calciner has a riser pipe through which exhaust gases from the rotary kiln flow. The gas offtake probe is arranged in a calciner nozzle, which is formed by a nozzle-like constricted section of the riser pipe, wherein the gas offtake probe is arranged flush on the calciner nozzle of the riser pipe.

9 Claims, 10 Drawing Sheets

(51) Int. Cl.
  *F27D 19/00* (2006.01)
  *B01F 15/06* (2006.01)
  *G01N 1/22* (2006.01)
  *F27B 7/42* (2006.01)

(52) U.S. Cl.
  CPC .... *G01N 33/0004* (2013.01); *B01F 2015/062* (2013.01); *B01F 2215/0047* (2013.01); *F27D 2019/0015* (2013.01); *G01N 2001/2235* (2013.01)

(58) Field of Classification Search
  CPC ........ F27D 2019/0015; G01N 33/0004; G01N 2001/2235
  See application file for complete search history.

(56) References Cited

U.S. PATENT DOCUMENTS

| | | | | |
|---|---|---|---|---|
| 4,249,892 A * | 2/1981 | Brachthauser | C04B 7/434 | 106/759 |
| 4,295,823 A * | 10/1981 | Ogawa | C04B 7/43 | 106/745 |
| 4,323,397 A * | 4/1982 | Herchenbach | F27B 7/2033 | 106/754 |
| 4,353,750 A * | 10/1982 | Quittkat | C04B 7/434 | 106/744 |
| 4,425,092 A * | 1/1984 | Brachthauser | F27B 7/2033 | 34/93 |
| 4,715,811 A * | 12/1987 | Lawall | F27B 7/2033 | 432/106 |
| 4,747,879 A * | 5/1988 | Wolter | F27B 7/2033 | 106/756 |
| 5,098,285 A * | 3/1992 | Bauer | C04B 7/4438 | 110/246 |
| 5,122,190 A * | 6/1992 | von Seebach | C04B 2/10 | 106/758 |
| 5,156,676 A * | 10/1992 | Garrett | C04B 7/4438 | 106/745 |
| 5,226,774 A * | 7/1993 | Tutt | F23G 5/20 | 414/149 |
| 5,339,751 A * | 8/1994 | Tutt | C04B 7/4438 | 110/186 |
| 5,364,265 A * | 11/1994 | Paliard | F27B 7/2033 | 432/106 |
| 5,816,795 A * | 10/1998 | Hansen | F27B 7/2033 | 110/246 |
| 5,992,041 A * | 11/1999 | McClaine | B01J 8/006 | 34/178 |
| 6,050,203 A * | 4/2000 | Reese | C04B 7/4407 | 110/226 |
| 6,050,813 A * | 4/2000 | Doumet | C04B 7/364 | 106/758 |
| 6,068,826 A * | 5/2000 | Maury | B01D 5/0096 | 106/745 |
| 6,325,620 B1 * | 12/2001 | Heinemann | C04B 7/364 | 110/345 |
| 6,345,981 B1 * | 2/2002 | Hansen | C04B 7/432 | 110/246 |
| 6,383,283 B1 * | 5/2002 | Doumet | C04B 7/364 | 106/743 |
| 6,484,416 B1 * | 11/2002 | Rawe | C04B 7/40 | 34/209 |
| 6,773,259 B1 * | 8/2004 | Bech | F27B 7/2025 | 432/14 |
| 8,328,550 B2 * | 12/2012 | Gasser | C04B 7/4446 | 432/14 |
| 9,121,639 B2 * | 9/2015 | Hammerich | F16K 3/029 | |
| 2003/0023127 A1 * | 1/2003 | Yamamoto | A62D 3/34 | 106/745 |
| 2004/0071620 A1 * | 4/2004 | Hawks | B01D 53/504 | 423/243.08 |
| 2005/0274067 A1 * | 12/2005 | Morton | C04B 7/4407 | 44/606 |
| 2007/0178418 A1 * | 8/2007 | Meyer | C04B 7/47 | 432/14 |
| 2007/0184396 A1 * | 8/2007 | Lowes | F27D 7/04 | 432/58 |
| 2008/0092781 A1 * | 4/2008 | Ramirez Tobias | C04B 7/345 | 106/767 |
| 2008/0245275 A1 * | 10/2008 | Mohr | C04B 7/436 | 106/739 |
| 2009/0193968 A1 * | 8/2009 | Jepsen | B01D 53/06 | 95/134 |
| 2010/0083878 A1 * | 4/2010 | Komatsu | B01D 45/12 | 106/751 |
| 2011/0126738 A1 * | 6/2011 | Kupper | C04B 7/361 | 106/743 |
| 2012/0045728 A1 * | 2/2012 | Hundebol | C04B 7/361 | 432/4 |
| 2013/0224673 A1 * | 8/2013 | Tiernan | F23G 5/444 | 432/105 |
| 2014/0120486 A1 * | 5/2014 | Sakaniwa | C04B 7/60 | 432/72 |
| 2014/0366499 A1 * | 12/2014 | Sakaniwa | B01D 53/68 | 55/434.2 |

FOREIGN PATENT DOCUMENTS

| | | | |
|---|---|---|---|
| JP | 4998639 B1 | 8/2012 | |
| WO | 2010049836 A1 | 5/2010 | |
| WO | WO 2010/049836 * | 5/2010 | ............... G01N 1/22 |

OTHER PUBLICATIONS

International Search Report re PCT/EP2013/073055, dated Feb. 14, 2014, 2 pages.

\* cited by examiner

CEMENT PRODUCTION SYSTEM

CROSS-REFERENCE TO RELATED APPLICATIONS

This application is the United States national phase of International Application No. PCT/EP2013/073055 filed Nov. 5, 2013, and claims priority to German Patent Application No. 10 2012 110 653.3 filed Nov. 7, 2012, the disclosures of which are hereby incorporated in their entirety by reference.

BACKGROUND OF THE INVENTION

Field of the Invention

The invention relates to a cement production plant having a preheater for preheating cement raw meal, a calciner for precalcining the preheated cement raw meal and a rotary tube furnace for firing the precalcined cement raw meal, wherein the calciner has a riser tube line through which the exhaust gases from the rotary tube furnace flow and which has a calciner nozzle.

Description of Related Art

Tremendous amounts of fuel are necessary for cement production. Efforts are therefore made to optimize the combustion process by, inter alia, analyzing the composition of the furnace exhaust gases and taking this into account in controlling the combustion process. In this way, it is possible to avoid dangerous operating conditions, reduce pollutants and improve the product quality. Protection against caked material is also an important point. The taking off of the gas was in the past and is sometimes also today carried out via long, water-cooled lances which are pushed from the side into the furnace inlet housing and project to before the furnace inlet seal. Although this is still the best position from a process engineering point of view, the lances are there subjected to high wear because of the ever higher thermal stress and the increased use of secondary fuels, so that the availability becomes ever lower and the maintenance requirements become ever higher. A change has therefore been made to carry out the measurements in the gas line adjoining the furnace inlet housing.

In WO 2010/049836 A1, the gas is taken off in the lower region of the riser tube line of the calciner. For this purpose, the gas is fed to a gas analysis instrument via a gas offtake port which is joined flush to the riser tube line. Although the wear is significantly lower compared to the lances projecting to the riser tube line as a result of the flush arrangement, it has also been found that a significantly greater measurement accuracy has to be accepted here.

DE 299 24 941 U1 relates to a plant for carrying out a process for firing pulverulent raw material, which has a cyclone preheater, a calciner, a furnace and a cooler, with an analytical measuring instrument for the process gases being arranged in the connecting line between furnace and calciner. Furthermore, DE 10 2008 036 088 B4 describes a process for operating a cement plant having a preheating zone, calcination zone and sintering zone, with a gas analysis being carried out in the inlet region of the sintering zone, the calcination zone and/or upstream of the beginning of the preheating zone.

SUMMARY OF THE INVENTION

It was therefore an object of the invention to improve the gas measurement so that firstly the gas offtake probe is subjected to very low wear stress and secondly gas analyses can be carried out with high measurement accuracy.

According to the present invention, the gas offtake probe is arranged on the calciner nozzle which is formed by a section of the riser tube line which is constricted in a nozzle-like manner, where the gas offtake probe is additionally joined flush to the riser tube line.

As a result of the flush arrangement, the gas offtake probe is subjected to comparatively low wear. In addition, it has been found that the measurement accuracy in the case of a flush arrangement on the calciner nozzle is significantly higher compared to a flush arrangement outside the nozzle.

This can be explained by the higher gas velocity in the calciner nozzle, with the velocity in the vicinity of the wall being even higher than in the middle. In addition, the usually relatively rough interior surface of the riser tube line leads to any thin, laminar boundary layers being dispersed by microturbulences and the resulting turbulence leading to transverse mixing which allows representative offtake of gas. The invention is therefore based on the synergistic action of the flush arrangement in combination with the installation position in the calciner nozzle.

In a preferred embodiment, the gas offtake probe is arranged in the region of the smallest cross section of the riser tube line. In addition, it can open either horizontally or obliquely into the riser tube line. In the case of horizontal offtake, the sucking-in of dust is minimal since both the dust entrained in the combustion air and also any particles falling down in countercurrent have a vector of travel which is orthogonal to the offtake of gas. In the case of an oblique, downward-directed gas offtake probe, gravity aids the discharge of the pneumatically cleaned-off dust from the gas offtake probe. If it is, on the other hand, directed upward, the introduction of dust particles from the combustion air is countered, with the discharge of dust impurities being more difficult.

The gas offtake probe is part of a gas offtake apparatus which has at least one filter unit in order to discharge the dust taken off. The filter unit can be provided axially or radially relative to the gas offtake probe. The axial arrangement makes an overall simpler construction possible and a lower level of deposits is to be expected because of the flow conditions. Cleaning-off of the probe tube is also more effective than in the case of a radial filter arrangement. Although in the case of the radial arrangement a somewhat less favorable flow of the drawn-in gas has to be accepted, cleaning-off is simpler since the particles cleaned off drop down under gravity and can subsequently be blown pneumatically out of the gas offtake tube. In addition, in the case of a radial arrangement, the gas offtake tube can be "poked free" if necessary through a rear axial opening without the filter being taken out. The gas offtake apparatus can also have a cooling system for cooling the gas offtake probe and/or a flushing unit for cleaning the filter unit.

In a further embodiment of the invention, the gas offtake probe is equipped with a gas offtake port which tapers conically into the riser tube line. The gap between the gas offtake port and the gas offtake probe becomes blocked with particles from the combustion air and partly deacidified raw meal over the course of time. Since this material leads to caked material, disassembly of a conically configured gas offtake port is made considerably easier since lower frictional forces occur and the probe can thus be pulled out of the port with a lower application of force.

In a further embodiment, the gas offtake apparatus is equipped with two gas offtake probes so that continuous gas analysis is made possible. In addition, the availability of the gas analysis system is increased.

Further advantages and embodiments of the invention are described below with the aid of the description and the drawings.

BRIEF DESCRIPTION OF THE DRAWINGS

The drawings show

DESCRIPTION OF THE INVENTION

Figure 1:
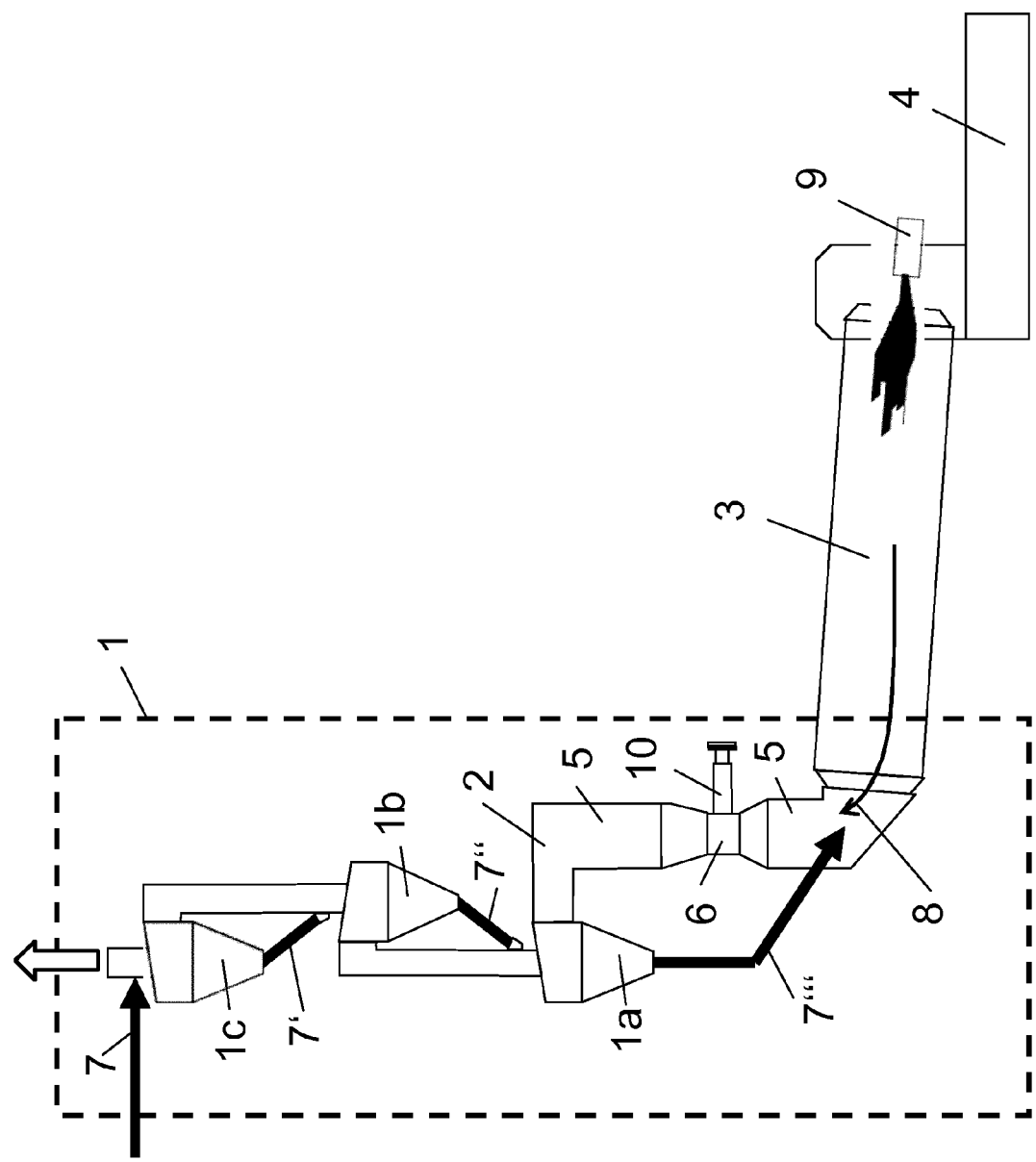
FIG. 1 a schematic depiction of a cement production plant.

The cement production plant shown in FIG. 1 consists essentially of a preheater 1 for preheating cement raw meal 7, a calciner 2 for precalcining the preheated cement raw meal, a rotary tube furnace 3 for firing the precalcined cement raw meal and a cooler 4 for cooling the fired cement clinker.

The preheater in this case is configured as an entrained flow preheater having a plurality of cyclone stages 1a, 1b, 1c and the exhaust gases 8 from the rotary tube furnace 3 flow through it in a known way. The preheater can of course comprise further cyclone stages, in particular from 4 to 5 cyclone stages.

The calciner has a riser tube line 5 with a calciner nozzle 6 through which the exhaust gases from the rotary tube furnace 3 likewise flow, where the calciner nozzle is formed by a section of the riser tube line which is constricted in a nozzle-like manner.

During operation, cement raw meal 7 is introduced in the upper region of the preheater 1 and travels successively through the individual stages of the preheater. The preheated cement raw meal 7' precipitated in the cyclone 1c is introduced into the gas line of the cyclone 1b and preheated further (7") and fed to the cyclone stage 1a. The hot cement raw meal 7''' is fed in the lower region of the riser tube line 5 into the calciner 2: the fine fraction of the preheated cement raw meal 7''' is there carried upward by the hot exhaust gases 8 from the rotary tube furnace into the cyclone 1a. Further fuel may optionally be fed into the calciner, so that the raw meal is precalcined in the calciner 2. In the cyclone 1a, the precalcined raw meal 7''' is precipitated again and subsequently goes into the rotary tube furnace 3 where it is fired to produce cement clinker. The thermal energy required is provided by combustion of fuel in a burner 9. The exhaust gases 8 formed leave the rotary tube furnace 3 in countercurrent to the precalcined raw meal and flow through the calciner 2 and subsequently the preheater 1. The fired cement clinker is finally cooled in the cooler 4.

The gas is taken off via a gas offtake probe 10 which is part of a gas analysis system and opens into the calciner nozzle 6. FIGS. 2 to 10 show various embodiments of the gas analysis system; various gas offtake apparatuses are firstly shown in FIGS. 2 to 7 and various gas analysis apparatuses are explained in more detail in FIGS. 8 to 10.

Figure 2:
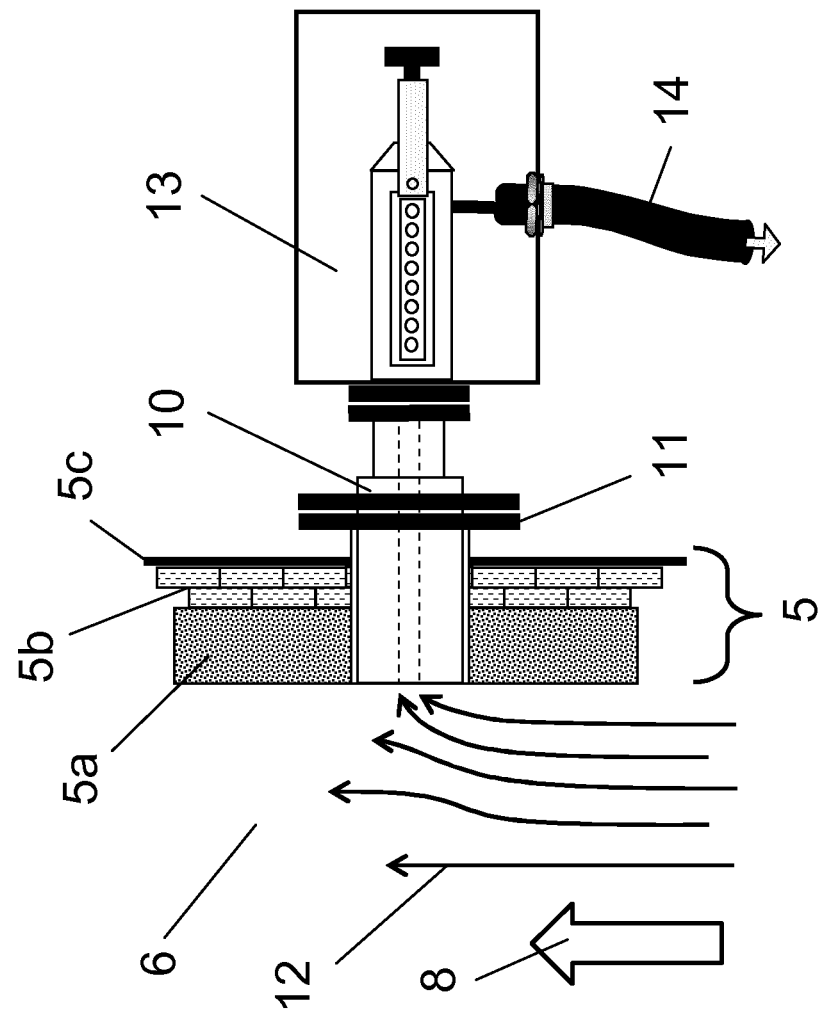
FIG. 2 a sectional view of a gas offtake probe with axial filter.

FIG. 2 shows a section of the calciner nozzle 6. It can be seen that the wall of the riser tube line is formed, from the inside outward, by a refractory inner wall 5a, a plurality of insulation layers 5b and an outer wall 5c consisting of steel. The gas offtake probe 10 is arranged via a gas offtake port 11 horizontally to the vertical riser line, with the gas offtake probe 10 being joined flush to the riser tube line. It is flush with the inner wall 5a so that it does not project into the stream of the exhaust gas 8. The gas offtake apparatus additionally has a filter device 13 which is arranged axially to the gas offtake probe 10 in the example depicted. In the filter unit 13, the exhaust gas 8 drawn off in the region of the calciner nozzle 6 is freed of entrained dust and fed via a preferably heated gas line 14 to a gas analysis instrument.

Figure 3:
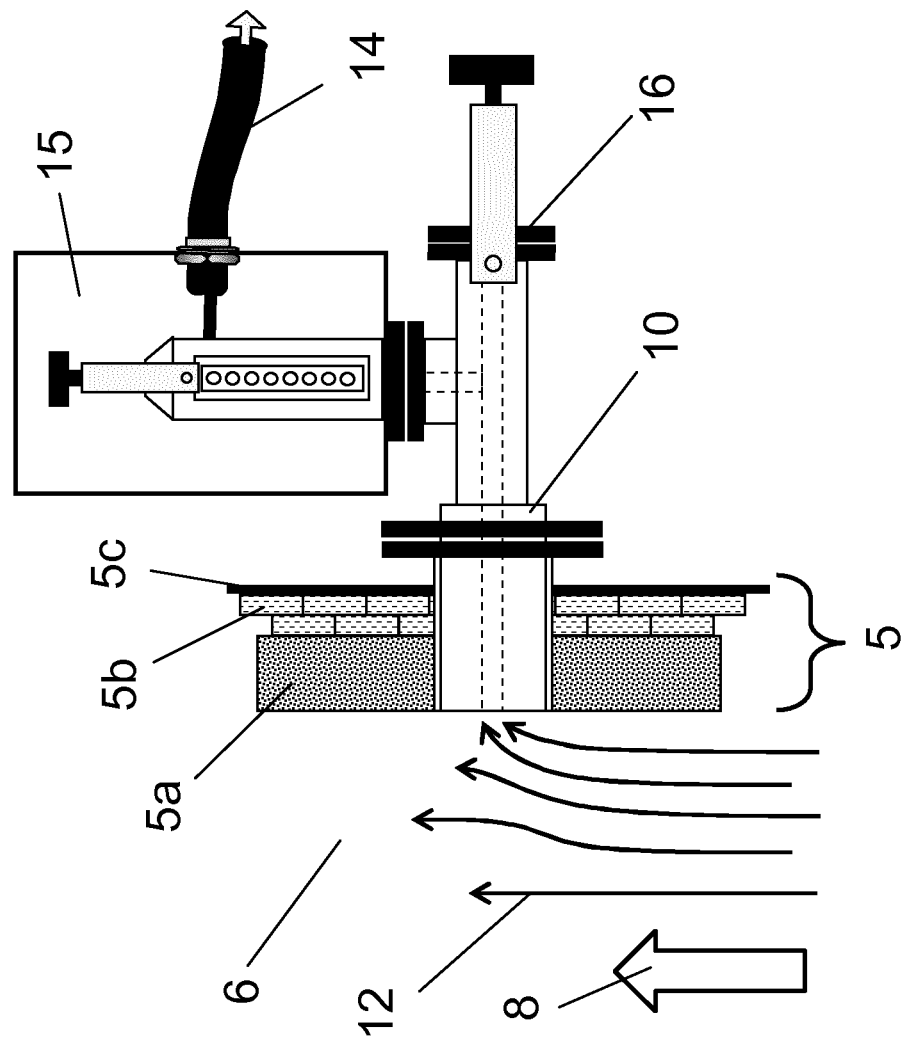
FIG. 3 a sectional view of a gas offtake probe with radial filter.

In the example as per FIG. 3, a radially arranged filter unit 15 is provided. The axial arrangement as per FIG. 2 has a simpler construction and a lower level of deposits is to be expected due to the axially directed flow conditions. Furthermore, axially directed cleaning of the gas offtake probe 10 is more effective. The construction of any heating of the exposed regions from the gas offtake probe 10 to the gas discharge line 14 is simpler compared to the radial arrangement in FIG. 3.

Although the radial arrangement as per FIG. 3 displays somewhat less favorable flow conditions for the exhaust gas drawn in, the cleaning-off of the filter unit 15 is easier since the cleaned-off particles drop downward under gravity and can be blown out pneumatically there. Furthermore, it is possible for the gas offtake probe to be "poked free" through a rear, axial opening (16) without the filter having to be removed.

Figure 4:
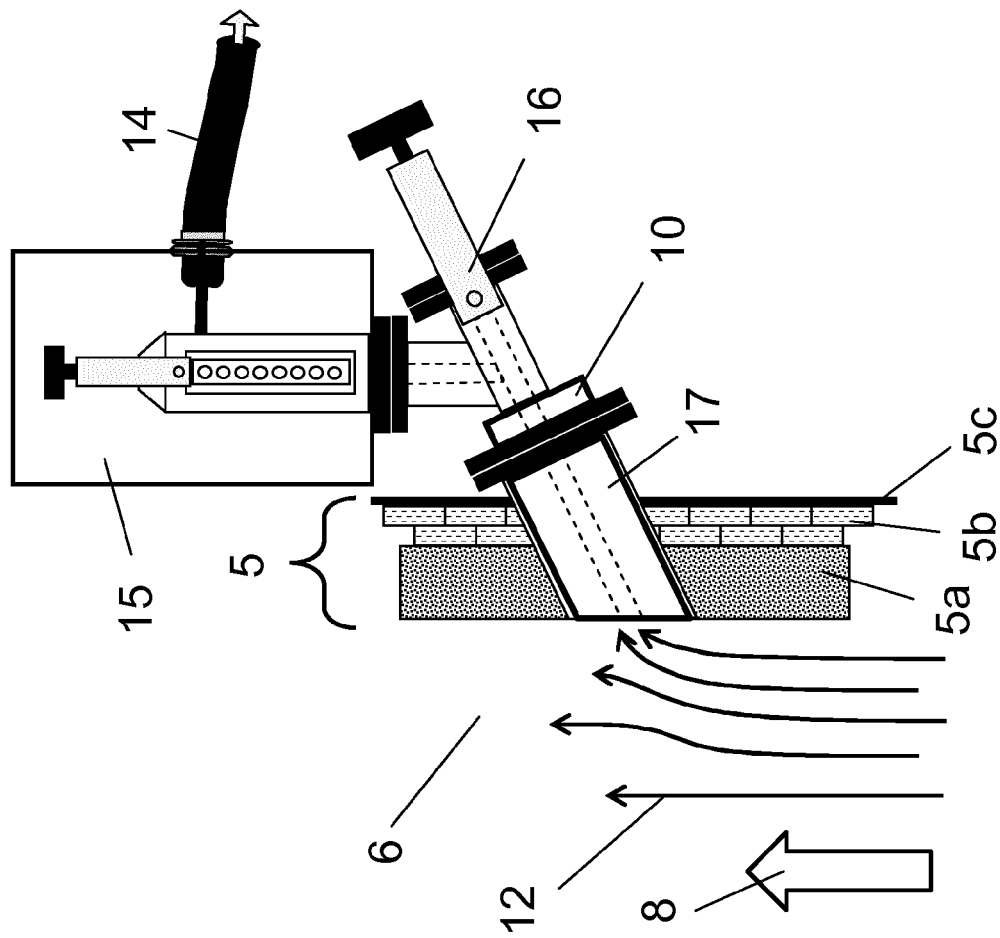
FIG. 4 a schematic sectional view of a gas offtake probe with filter unit opening obliquely downward into the riser tube, FIG. 5 a schematic sectional view of a gas offtake probe with filter unit opening obliquely upward into the riser tube, FIG. 6 a schematic sectional view of a gas offtake probe with conical gas offtake port, FIG. 7 a schematic depiction of a gas offtake apparatus with flushing unit and cooling system, FIG. 8 a schematic depiction of a gas analysis system with an in-line gas analysis instrument, FIG. 9 a schematic depiction of a gas offtake apparatus having two gas offtake probes and a gas analysis instrument, FIG. 10 a schematic depiction of the gas analysis instrument belonging to FIG. 9.
Figure 5:
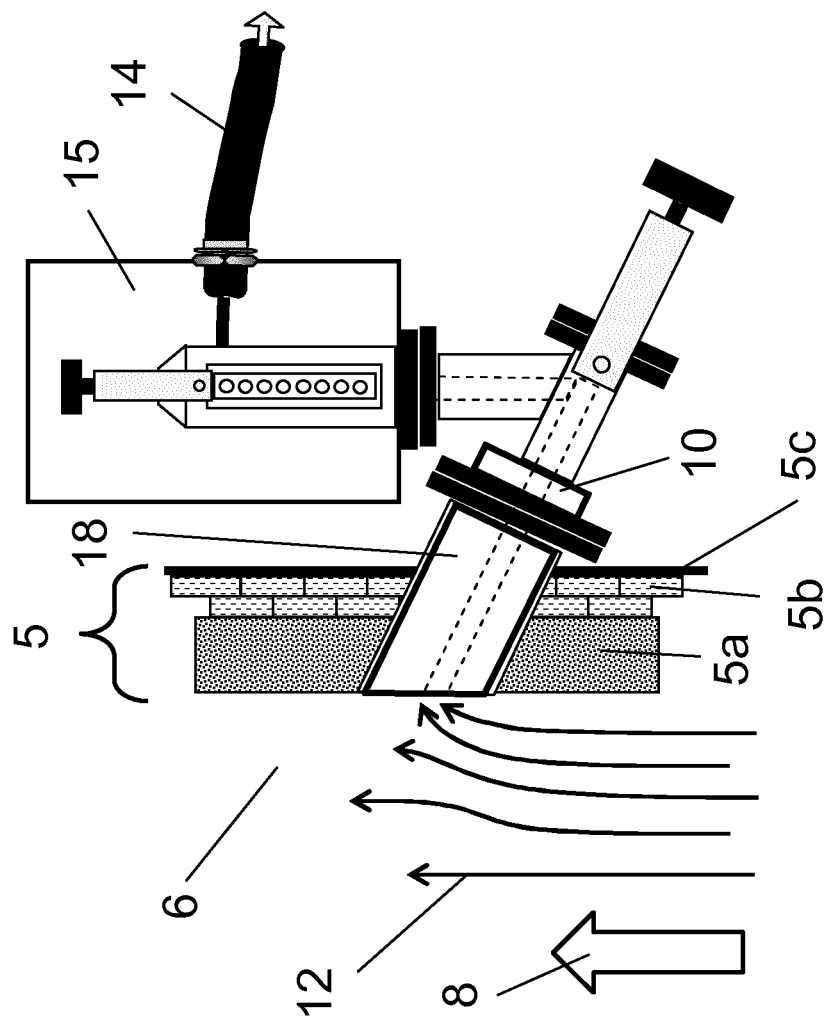

FIGS. 4 and 5 show two examples with obliquely directed gas offtake ports 17, 18, so that the gas offtake probes 10 held in the gas offtake ports correspondingly open obliquely into the riser tube line 5. In the case of horizontal offtake as per the examples of FIGS. 2 and 3, minimal sucking-in of dust is to be expected since both the dust entrained in the exhaust gas and any particles falling down from above in countercurrent have a vector of travel which is orthogonal to the offtake of the gas.

In the example as per FIG. 4, the gas offtake probe opens obliquely downward into the riser tube line 5 and thereby aids the discharge under gravity of the pneumatically cleaned-off dust from the gas offtake probe. On the other hand, if the gas offtake probe 10 is directed obliquely upward (FIG. 5), dust particles from the combustion air can be introduced less readily. However, it has to be accepted that the discharge of dust during cleaning operations is more difficult.

Figure 6:
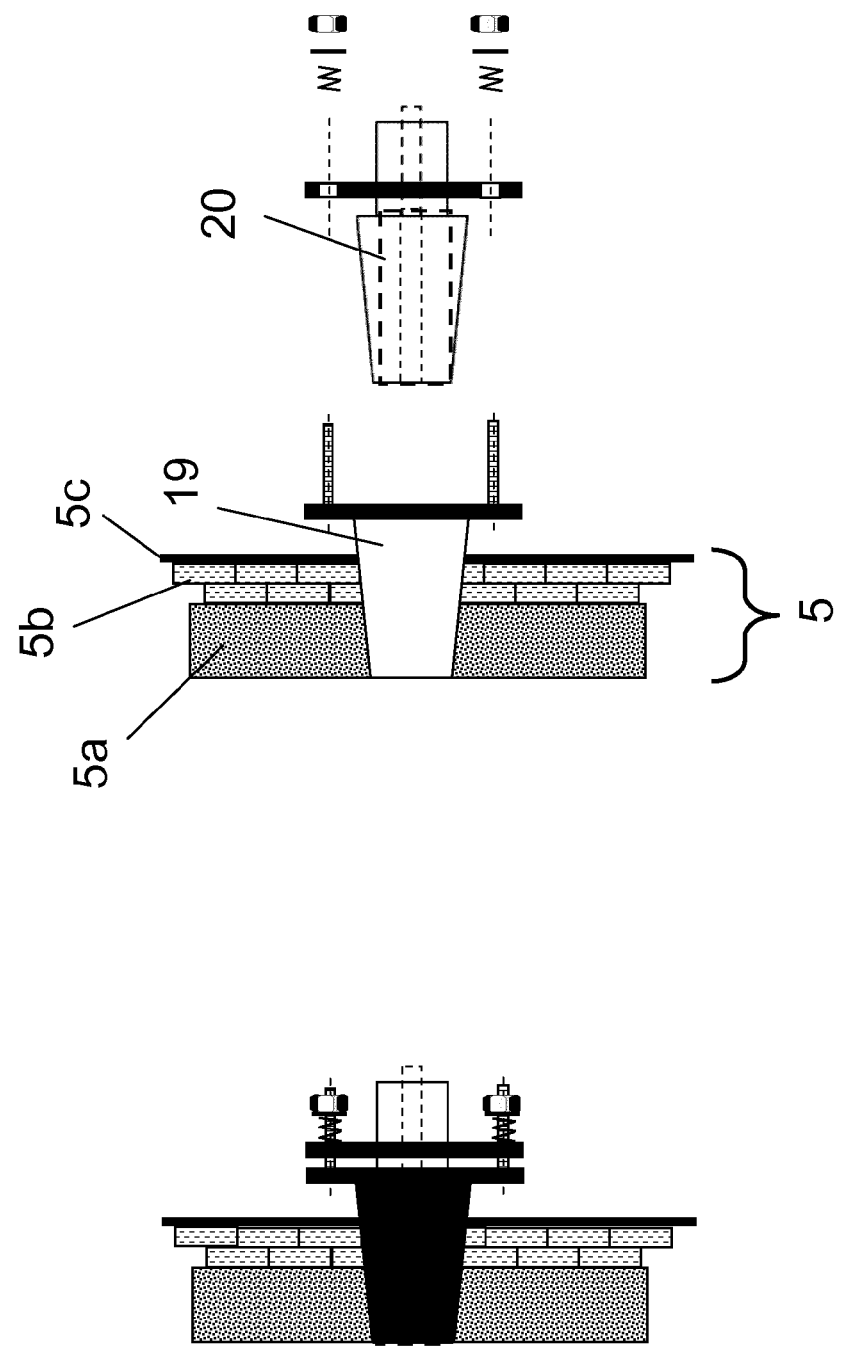

In the example of FIG. 6, a conical gas offtake port 19 for attachment of a correspondingly conical gas offtake probe 20 is shown. The outer conical shape of the gas offtake port 19 makes removal of the gas offtake probe 20 for maintenance work considerably easier. The gap between the gas offtake port 19 and the gas offtake probe 20 will become blocked by particles from the combustion air and partly deacidified raw meal over the course of time. In addition, the material tends to cake, so that the gas offtake probe can only be pulled out with increased application of force. However, as a result of the conical shape of the gas offtake port 19, the frictional forces occurring in demounting are lower, so that the gas offtake probe can be pulled out of the port with correspondingly lower application of force.

Figure 7:
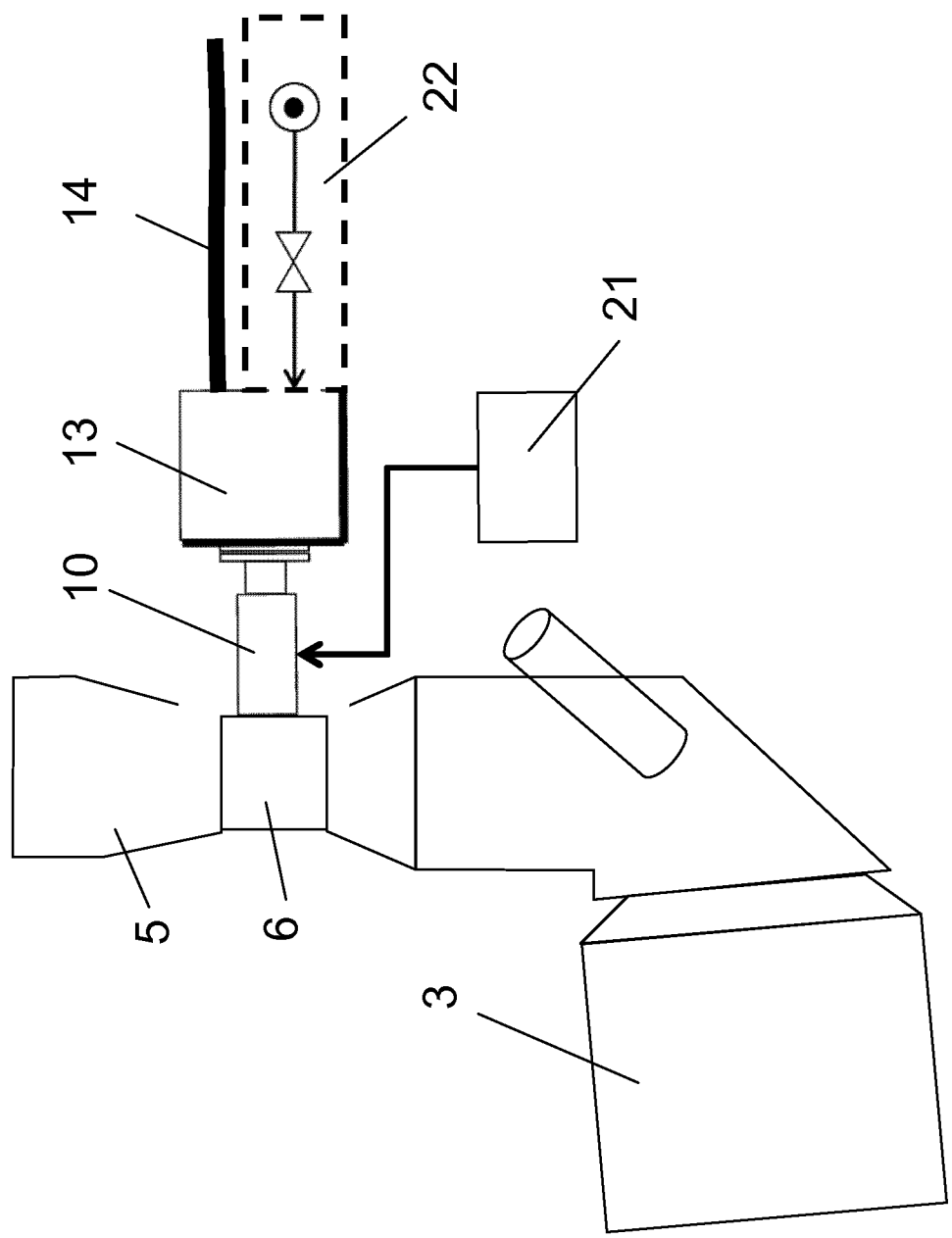

In addition to the gas offtake probe and the filter unit, the gas offtake apparatus as per FIG. 7 also has a cooling system 21 for cooling the gas offtake probe 10. The filter unit 13 can additionally be equipped with a backflushing unit 22 for cyclic cleaning of the filter unit. Of course, the other examples as per FIGS. 2 to 6 can also be equipped with an appropriate cooling system 21 and a backflushing unit 22.

Figure 8:
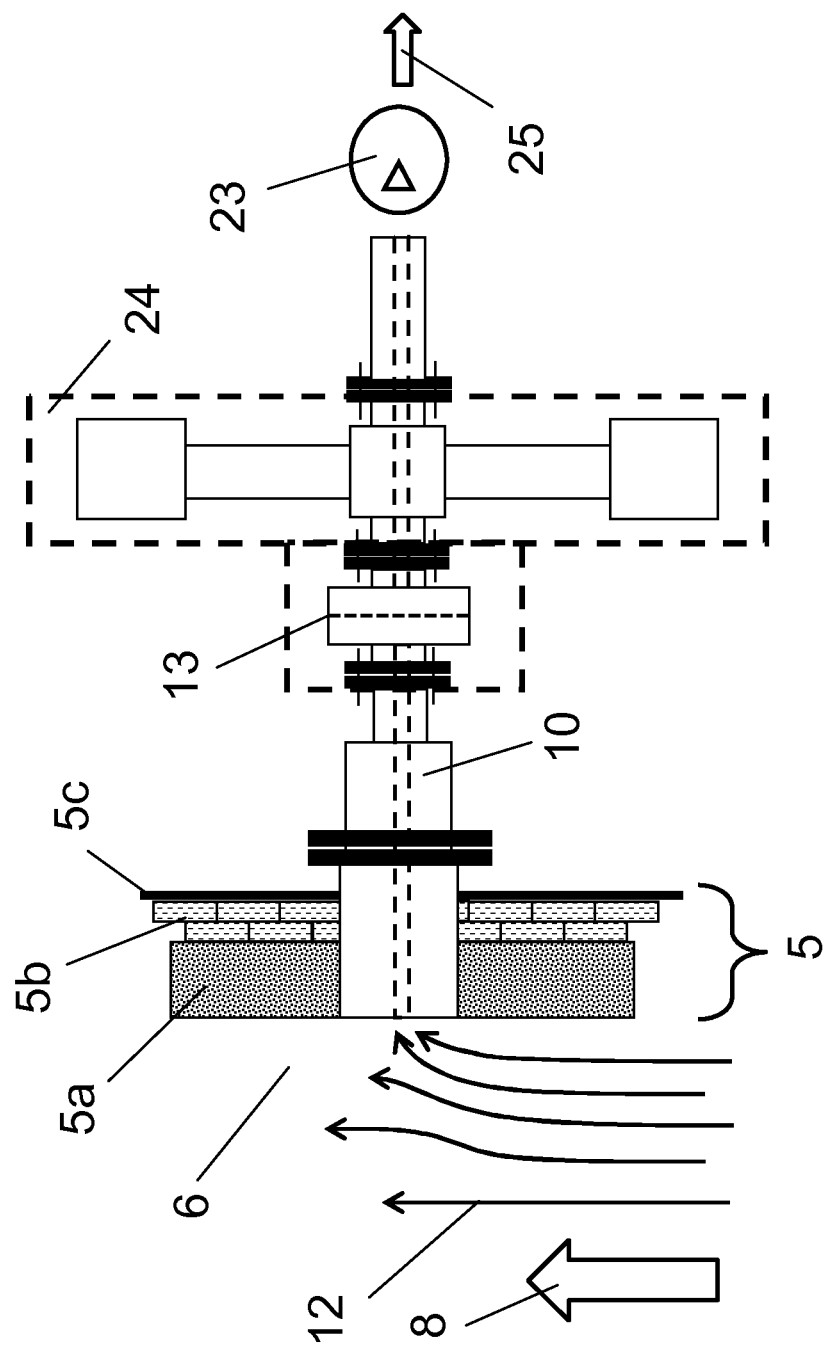

The in-line gas analysis system shown in FIG. 8 has a gas analyzer 24. The gas to be analyzed is taken off by means of the gas offtake probe 10 from the calciner nozzle 6 by means of a gas transport unit 23, for example a pump, and analyzed in the gas analyzer 24 which also contains the filter unit 13. The analyzed gas leaves the gas analysis system through a gas outlet 25.

Figure 9:
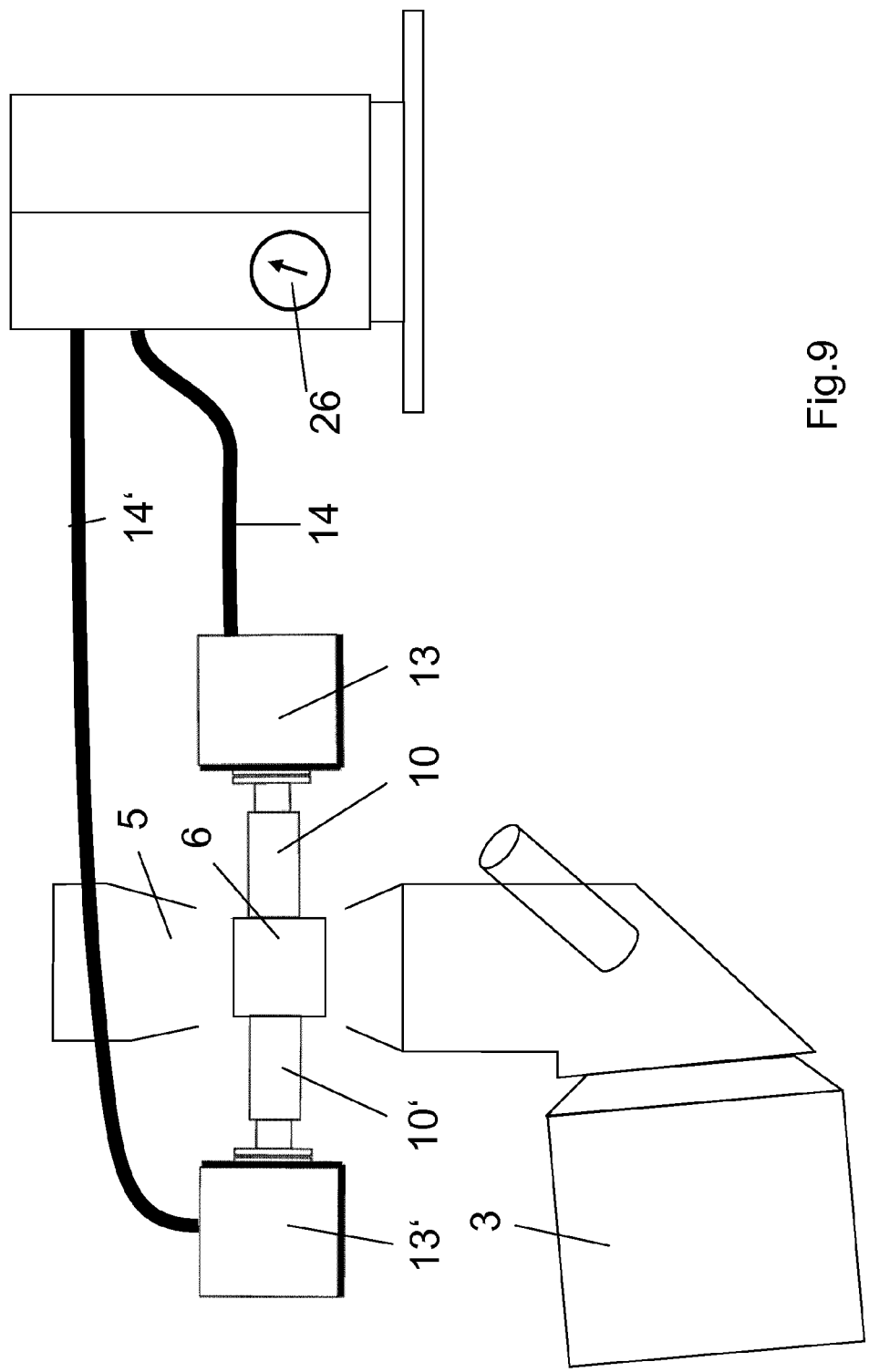

Furthermore, it is possible to provide a gas analysis system having a plurality of, in particular two, gas offtake probes 10, 10' which are each connected to a filter unit 13, 13' (see FIG. 9). The gas to be analyzed is taken off from the calciner nozzle by means of one of the two gas offtake probes 10, 10', filtered and fed via the optionally heated gas line 14, 14' to a gas analyzer 26. The optional second gas offtake system makes continuous gas analysis without interruption of the measurement signal possible. The availability of the gas analysis system is also increased thereby. The gas taken from the calciner nozzle 6 via the selected gas offtake probe 10, 10' is filtered and fed via the optionally heated gas line 14, 14' to the gas analyzer 26. The optional second gas offtake system makes continuous gas analysis without interruption of the measurement signal possible.

Figure 10:
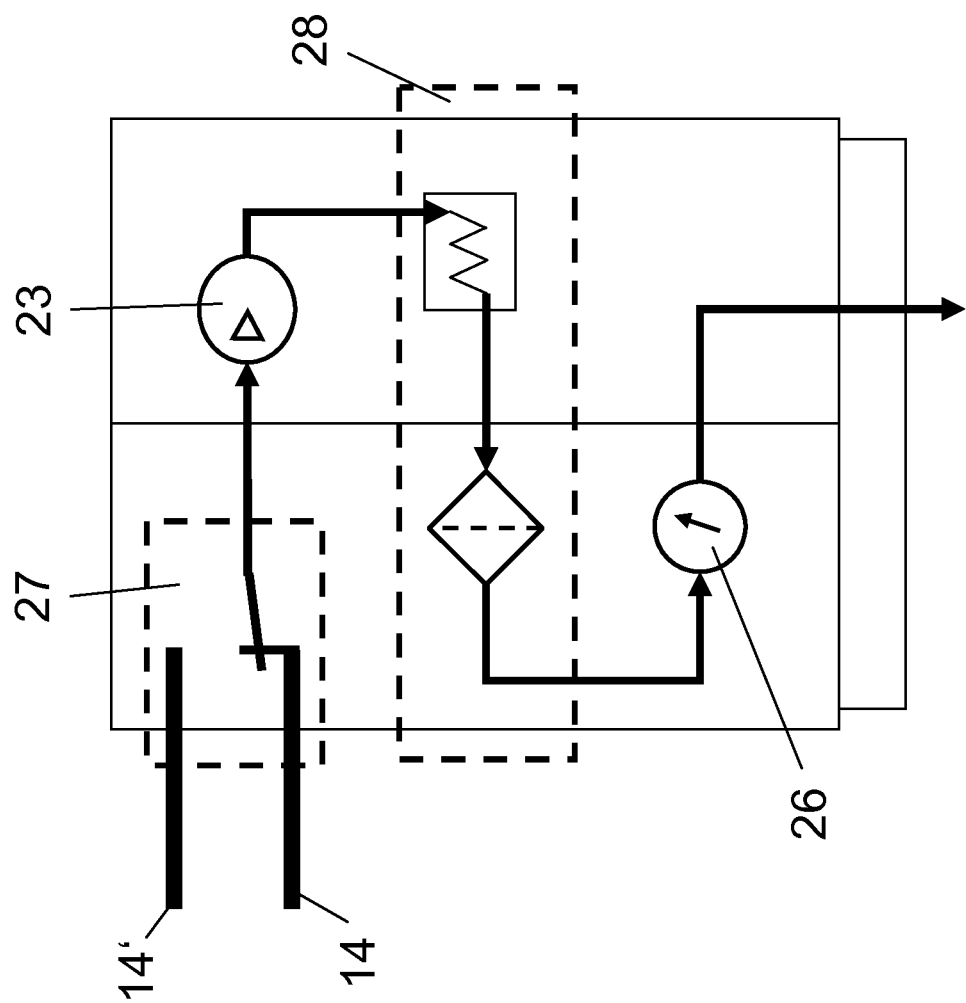

FIG. 10 shows the gas analysis system of FIG. 9 in more detail. The gas lines 14, 14' connected to the two gas offtake probes 10, 10' can firstly be selected via a switching unit 27. The gas taken off from the selected gas offtake system is conveyed in the heated gas line 14 or 14' via the gas transport unit 23 to a gas treatment unit 28 and conditioned there for the gas analyzer 26. The actual analysis then takes place in the gas analyzer 26.

To obtain an unfalsified measurement result, the backflushing unit 22 shown in FIG. 7 is necessary. This means that the supply of gas to the gas analyzer 26 is interrupted during a cleaning operation and a reliable analysis result can be produced again only when the flushing gas has completely left the system, with this operation being able to take a few minutes. During this time, the second gas offtake probe is used in order to achieve a continuous analysis result. The cleaning intervals for the two gas offtake probes are therefore adapted to one another. A further advantage is that even when a gas offtake probe has to be serviced or replaced in another way, the other gas offtake probe always continues to be available for gas analysis. When two gas offtake probes are used, the gas analysis can be carried out in three different modes of operation, with either only the probe 1 or only the probe 2 or both probes being operated alternately.

The invention claimed is:

1. A cement production plant comprising:
   a preheater for preheating cement raw meal,
   a calciner for precalcining the preheated cement raw meal,
   a rotary tube furnace for firing the precalcined cement raw meal,
   wherein the calciner has a riser tube line having a calciner nozzle comprising an exterior wall and an interior wall and through which exhaust gases from the rotary tube furnace flow,
   wherein the calciner nozzle is formed by a section of the riser tube line which is constricted into a nozzle form, and
   wherein at least one gas offtake probe which is arranged flush on the interior wall of the calciner nozzle of the riser tube line at a point or plane of smallest cross section of the riser tube line.

2. The cement production plant as claimed in claim 1, wherein the gas offtake probe opens horizontally into the riser tube line.

3. The cement production plant as claimed in claim 1, wherein the gas offtake probe opens obliquely into the riser tube line.

4. The cement production plant as claimed in claim 1, wherein the gas offtake probe is part of a gas offtake apparatus which has at least one filter unit.

5. The cement production plant as claimed in claim 4, wherein the filter unit is arranged axially or radially relative to the gas offtake probe.

6. The cement production plant as claimed in claim 1, wherein the gas offtake probe is part of a gas offtake apparatus which has a cooling system for cooling the gas offtake probe.

7. The cement production plant as claimed in claim 1, wherein the gas offtake probe is equipped with a gas offtake port which tapers conically in the direction of the riser tube line, such that a first radius of the gas offtake port located at the interior wall of the calciner nozzle is smaller than a second radius of the gas offtake port located at the exterior wall of the calciner nozzle.

8. The cement production plant as claimed in claim 1, wherein at least two gas offtake probes which are joined flush to the riser tube line are provided on the calciner nozzle.

9. The cement production plant as claimed in claim 8, wherein the two gas offtake probes are connected to a joint gas analysis instrument.

* * * * *